(12) United States Patent
Turchetta et al.

(10) Patent No.: US 7,858,634 B2
(45) Date of Patent: Dec. 28, 2010

(54) AMORPHOUS 3-PYRIDIL-1- HYDROXYE-THYLIDEN-1,1- BIPHOSPHONIC ACID MONOSODIUM SALT AND PROCESS FOR THE PREPARATION THEREOF

(75) Inventors: Stefano Turchetta, Rome (IT); Pietro Massardo, Rome (IT); Umberto Ciambecchini, Rome (IT)

(73) Assignee: Chemi SpA, Milan (IT)

( * ) Notice: Subject to any disclaimer, the term of this patent is extended or adjusted under 35 U.S.C. 154(b) by 759 days.

(21) Appl. No.: 11/068,484

(22) Filed: Feb. 28, 2005

(65) Prior Publication Data

US 2005/0215793 A1    Sep. 29, 2005

Related U.S. Application Data

(60) Provisional application No. 60/558,908, filed on Apr. 1, 2004.

(30) Foreign Application Priority Data

Mar. 3, 2004    (IT) .......................... MI2004A0403

(51) Int. Cl.
*A61K 31/675* (2006.01)
(52) U.S. Cl. ........................................ 514/277; 546/22
(58) Field of Classification Search ................... 546/22; 514/277
See application file for complete search history.

(56) References Cited

U.S. PATENT DOCUMENTS

| | | | |
|---|---|---|---|
| 5,368,587 A * | 11/1994 | Lechleiter | .................... 604/416 |
| 5,756,737 A | 5/1998 | Turchetta et al. | |
| 6,583,287 B1 | 6/2003 | Rossi et al. | |
| 6,897,339 B2 | 5/2005 | Turchetta et al. | |
| 7,105,681 B2 | 9/2006 | Turchetta et al. | |
| 7,241,805 B2 | 7/2007 | Oberegger et al. | |
| 7,332,603 B2 | 2/2008 | De Ferra et al. | |
| 7,358,399 B2 | 4/2008 | Turchetta et al. | |
| 7,417,149 B2 | 8/2008 | Turchetta et al. | |
| 2005/0142185 A1* | 6/2005 | Beleno et al. | ................ 424/451 |

FOREIGN PATENT DOCUMENTS

| | | | |
|---|---|---|---|
| EP | 0186405 | * | 2/1986 |
| EP | 0186405 | * | 7/1986 |
| WO | WO-03/033508 A1 | | 4/2003 |
| WO | WO-03/086355 A1 | | 10/2003 |
| WO | WO-2005/082915 | | 9/2005 |

OTHER PUBLICATIONS

Howley's "condesed chemical dictionary" p. 68 (1997).*
Merck manuel "urollithiasis" (2008) internet print out 5 pages.*
Doelker et al. "Crystalline modification . . . " CA 138:209993 (2002).*
Perkins et al. "Esophagial transit . . . " Int. J. Pharm. 186, p. 169-175 91999).*
Lieberman et al. "Pharmaceutical dosage forms" p. 462-465 (1989).*
SSCI "screening for amorphous drug . . . " p. 1-3 (2003).*
SSCI "Amorphous solids . . . " p. 1-3 (2003).*
Exhibit I.*
Medical Device "Liphilization" (2009) p. 1 from internet.*
GEA "test center for lyophilization application support" p. 1-2 from internet (2009).*
Ma et al."Effects of . . . " Sci. Search AN04464647 Abstract (1995).*
Nakamura et al. "Osteoprotegrin . . . " Sci Search. AN 12263872, abstract (2003).*
Osteoporosis Prevention, Diagnosis, and Therapy, American Medical Association, 2001, vol. 285, No. 6, pp. 785-796.
M. Rossini, et al., "Effects of Oral Alendronate in Elderly Patients with Osteoporosis and Mild Primary Hyperparathyroidism," *Journal of Bone and Mineral Research*, 2001, Volume, No. 1, pp. 113-119.
S. Boonen, et al., "Age-Related (Type II) Femoral Neck Osteoporosis in Men: Biochemical Evidence for Both Hypovitaminiosis D- and Androgen Deficiency—Induced Bone Resporption," *Journal of Bone and Mineral Research*, 1997, vol. 12, No. 12, pp. 2119-2126.
M. Gupta, et al. "Inhibition of calcium oxalate urolithiasis in a rat model of lithogenesis using bisphosphonates," *J Endourol.*, 1997; 11(1):1-4 (ISSN: 0892-7790).
Gambacorta, A., et al.; "Silica Supported Tetrabutylammonium Fluoride as a Catalyst for the Silylation of Carbonyl and Hydroxy Compounds with Ethyltrimethylsilylacetate"; Synth. Commun.; 1989; pp. 2441-2448.
Gambacorta, A., et al.; "Bicyclo [3.3.1] Nonane Approach to Pinguisane Terpenoids, Total Synthesis of (±) Pinguisone"; Tetrahedron; 1988; vol. 44, No. 15; pp. 4837-4846.
Gambacorta, A., et al.; "Bicyclo [3.3.1] Nonanes as Synthetic Intermediates Synthesis of 1-Hydroxy-Anti-8-Acetylbicyclo [4.2.2] Decane"; Tetrahedron Letters; 1991; vol. 32, No. 46; pp. 6805-6808; 1991.
Gambacorta, A., et al.; "Synthesis of Substituted cis-Bicyclo [3.3.0] Octane-1-Carbonyl Derivatives by Stereospecific Rearrangement of 1-Chloro-9-Hydroxybicyclo [3.3.1] Nonanes"; Tetrahedron; 1991; vol. 47, No. 43; pp. 9097-9102.

* cited by examiner

*Primary Examiner*—Celia Chang
(74) *Attorney, Agent, or Firm*—Lucas & Mercanti, LLP

(57) ABSTRACT

A process for the preparation of 3-pyridil-1-hydroxyethyliden-1,1-biphosphonic acid monosodium salt of formula

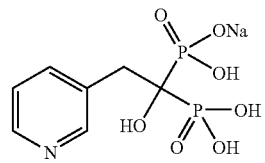

in an amorphous form, preferably lyophilized, and its pharmaceutical compositions are described. Said amorphous form, characterized by stability and simplicity of preparation and formulation, can be obtained by an industrially applicable lyophilization process, which comprises the steps of:
a) dissolving or suspending 3-pyridyl-1-hydroxyethyliden-1,1-biphosphonic acid in an aqueous solvent,
b) adding one equivalent of a base having sodium as cation
c) subjecting the solution to lyophilization.

16 Claims, 1 Drawing Sheet

AMORPHOUS 3-PYRIDIL-1-HYDROXYETHYLIDEN-1,1-BIPHOSPHONIC ACID MONOSODIUM SALT AND PROCESS FOR THE PREPARATION THEREOF

The present application claims priority to under 35 U.S.C. §119 to Italian Application No. MI2004A000403 filed Mar. 3, 2004, and to U.S. Provisional Application No. 60/558,908, filed Apr. 1, 2004, both of which are hereby incorporated by reference in their entirety.

The present invention relates to a process for the preparation of 3-pyridil-1-hydroxyethyliden-1,1-biphosphonic acid monosodium salt in an amorphous form, preferably lyophilized, the compound thus obtainable and its pharmaceutical formulations.

STATE OF THE ART

The monosodium salt of 3-pyridil-1-hydroxyethyliden-1,1-biphosphonic acid, also known with the name of sodium risedronate (Merck Index, 1996, n. 8396), is a drug used for the treatment of diseases related with calcium metabolism, of formula:

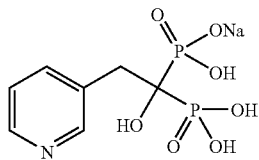

The free acid (risedronic acid), its pharmaceutical compositions and salts are mentioned, even if not specifically disclosed, in U.S. Pat. No. 5,583,122 while U.S. Pat. No. 6,410,520 describes the preparation and the characteristics of the sodium salt of the monohydrate and hemipentahydrate crystalline forms. WO03/086355, on the contrary, describes new polymorph crystalline forms of sodium risedronate. In the literature, as far as we know, sodium risedronate has never been described both in amorphous and in lyophilized forms, as this compound, has always been isolated in crystalline form.

It is known that some pharmaceutical compounds, in amorphous form, show improved bioavailability and adsorption with respect to crystalline forms, as described for example in WO03/033508 for sodium alendronate, of formula:

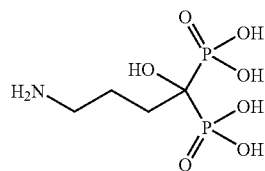

whose amorphous form is more rapidly dissolved in water than its crystalline forms.

We have now surprisingly found that, even for sodium risedronate, structurally different from sodium alendronate, the amorphous form, preferably lyophilized, presents improved water solubility and bioavailability with respect to the commercially available or otherwise described crystalline forms.

A comparative dissolution test between the amorphous form of sodium risedronate, object of the present invention, and the hemipentahydrate crystalline form prepared according to U.S. Pat. No. 6,410,520 has, in fact, been performed. From this test it results that after suspension of 200 mg of amorphous sodium risedronate at 20° C. in 25 ml of deionized water, under magnetic stirring at 25 rpm, complete dissolution is observed within 2', while an equal amount of sodium risedronate hemipentahydrate suspended in 25 ml of deionized water shows an undissolved residue even after 30'.

DESCRIPTION OF THE INVENTION

Figure 1:
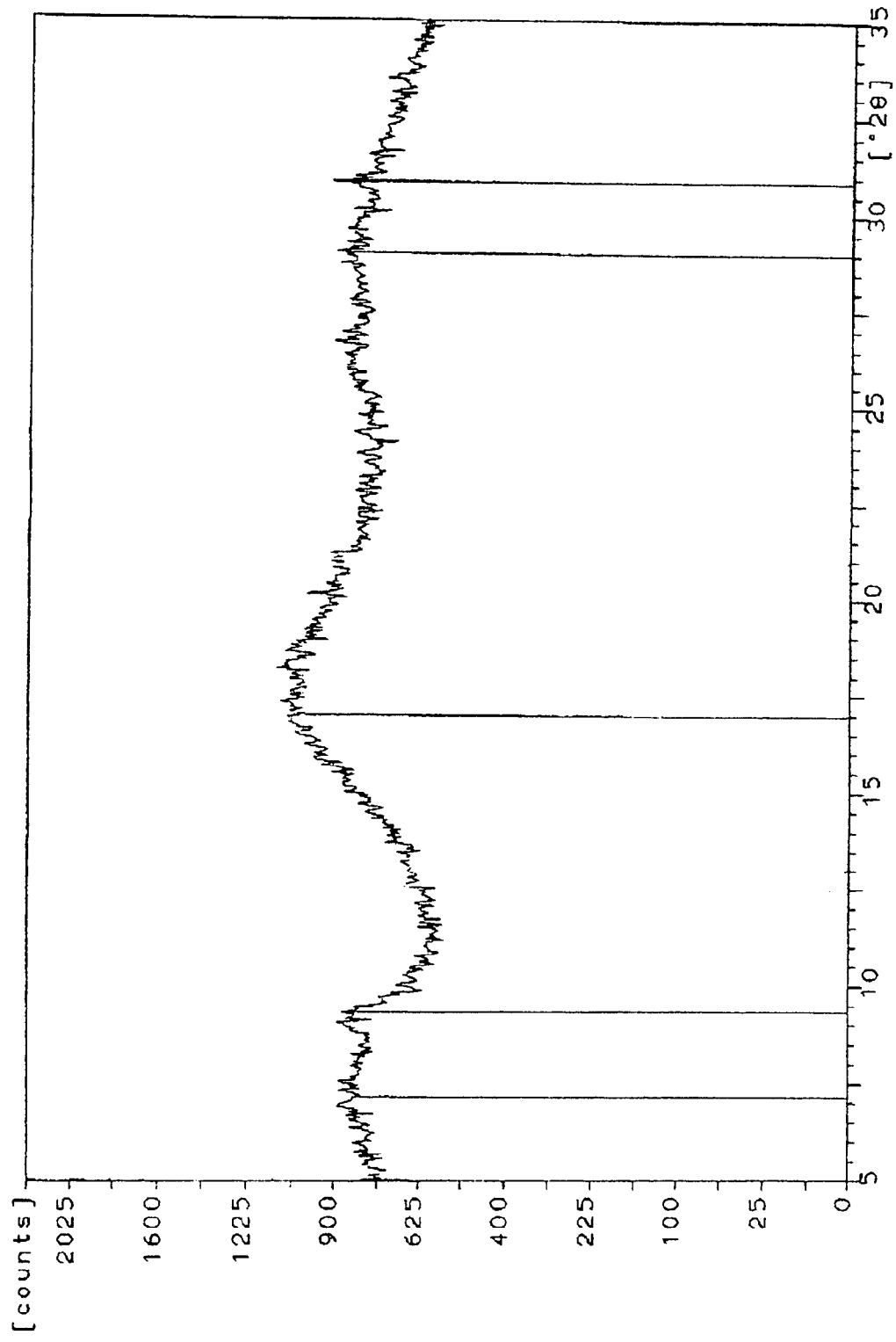
FIG. 1. X-ray diffraction spectrum of amorphous risedronate.

It is therefore a first object of the present invention sodium risedronate in amorphous form, characterized by an X-ray diffraction spectrum as represented in FIG. 1.

A process for the preparation of said sodium risedronate in amorphous form, its use for the manufacture of medicaments for the treatment of diseases deriving from calcium metabolism alterations and pharmaceutical compositions thereof are further objects of the present invention.

The process in object, of simple industrial applicability, includes the steps of:

a) suspending or dissolving risedronic acid in an aqueous solvent,
b) adding about one molar equivalent of a base having sodium as cation, such as for example sodium hydroxide, sodium carbonate, sodium phosphate and the like,
c) submitting the resulting solution to lyophilization.

An alternative process comprises the steps of:

a') dissolving sodium risedronate, in any crystalline form, in an aqueous solvent, and
c) submitting the resulting solution to lyophilization.

These processes allow the preparation of sodium risedronate in amorphous form, as confirmed by X-ray diffractogram of the powdered product, reported in FIG. 1.

The risedronic acid used in the process can be prepared by known techniques, for example as illustrated in the patent EP1243592.

In the above described procedures the aqueous solvent used for suspending or solubilizing risedronic acid or its sodium salt is, generally, water or admixtures of water and $C_1$-$C_6$ alcohols, such as for example methanol, ethanol, isopropanol, n-propanol, n-butanol, isobutanol, ter-butanol, n-pentanol and n-hexanol, more preferably ter-butanol.

The amorphous form, preferably lyophilized, of sodium risedronate, in particular, is obtainable according to the above described steps, by suspending or dissolving risedronic acid or its sodium salt in the selected solvent, solvent which is generally used in a ratio comprised between 500:1 and 10:1, preferably between 300:1 and 50:1, more preferably around 250:1, said ratio being expressed in ml of solvent per gram of risedronic acid.

The sodium-containing base can be selected among sodium hydroxide, sodium methylate, sodium carbonate, sodium phosphate, sodium bicarbonate, sodium acetate, preferably sodium carbonate or sodium hydroxide, and even more preferably sodium hydroxide.

Said base is added in an amount more or less equal to one molar equivalent. Consequently, the pH of the solution resulting from base addition is generally comprised between 4 and 5.

This solution is then charged into a lyophilizer and submitted to a lyophilization process.

The following preparative examples are now presented for illustrating some of the methods usable for manufacturing sodium risedronate in amorphous form, but they do not intend to limit the invention itself in any way.

Example 1

21.0 g of risedronic acid and 700 ml of deionized water are charged into a 1-liter reactor, equipped with mechanical stirrer and thermometer. The suspension, under stirring, is added with 148.4 ml of NaOH 0.5N thus obtaining complete dissolution of the suspended solid. The pH of the solution is 4.67. The solution is kept under stirring for 10' and filtered on a paper filter and put into Lioguard chambers. The chambers are introduced into a lyophilizer which is set according to the following parameters: a) freezing-phase: temperature −40° C., freezing time 3 hours; b) lyophilization phase: time 89 hours, internal temperature 30° C., residual vacuum 400÷450 μHg. At the end of the process, the white and soft product is discharged from the chambers. 20.9 g of lyophilized amorphous sodium risedronate are thus obtained (yields 92.3%).

Example 2

18.0 g of risedronic acid and 730 ml of deionized water are charged into a 1-liter reactor, equipped with mechanical stirrer and thermometer. The suspension, under stirring, is added with 3.4 g of $Na_2CO_3$. The admixture is kept under stirring for 30', up to complete dissolution of the undissolved solids. The solution, whose pH is 4.57, is filtered on a paper filter and put into Lioguard chambers. The chambers are introduced into a lyophilizer and processed according to example 1. At the end 17 g of lyophilized amorphous sodium risedronate are thus obtained (yields 87.6%).

Example 3

20.0 g of risedronic acid, 70 ml of deionized water and 100 ml of ter-butanol are charged into a 1-liter reactor, equipped with mechanical stirrer and thermometer. The suspension, under stirring, is added with 70.7 ml of 1M NaOH. The admixture is kept under stirring for 10', up to complete dissolution of the undissolved solids. The solution, whose pH is 4.60, is filtered on a paper filter and put into Lioguard chambers. The chambers are introduced into a lyophilizer and processed according to example 1. At the end 19.8 g of lyophilized amorphous sodium risedronate are thus obtained (yields 92.6%).

Example 4

10.0 g of sodium risedronate and 500 ml of deionized water are charged into a 1-liter reactor equipped with mechanical stirrer and thermometer. The suspension, under stirring, is heated at 60° C. and kept in that condition for two hours, up to complete dissolution. The mixture is filtered on paper filter and put into Lioguard chambers. The chambers are introduced into a lyophilizer and processed according to example 1. At the end 9.3 g of lyophilized amorphous sodium risedronate are thus obtained (yields 93%).

Example 5

200 mg of lyophilized amorphous sodium risedronate, 200 mg of anhydrous lactose and 5 mg of magnesium stearate are introduced in a mortar.

The powder is mixed and transferred into a Graseby Specac tabletting machine and compressed by applying a compression force of 5 tons. The described procedure is repeated ten times thus obtaining 10 identical tablets.

The invention claimed is:

1. A process for the preparation of sodium risedronate in amorphous form, comprising the steps of:
   a) suspending or dissolving risedronic acid in an aqueous solvent selected from the group consisting of water and an admixture of water and tert-butanol;
   b) adding a base having sodium as cation, wherein the pH of the resulting solution is between 4 and 5; and
   c) submitting the resulting solution to lyophilization, wherein the resulting sodium risedronate product is in powdered amorphous form.

2. The process according to claim 1, characterized in that the solvent of step a) is used in a ratio comprised between 500:1 and 10:1, said ratio being expressed in ml of solvent per gram of risedronic acid.

3. The process according to claim 1, characterized in that the base of step b) is selected among sodium hydroxide, sodium methylate, sodium carbonate, sodium bicarbonate and sodium acetate.

4. The process according to claim 3, characterized in that the base in step b) is sodium hydroxide.

5. The process according to claim 1, characterized in that the base is added in equimolar amount with respect to risedronic acid.

6. The process according to claim 2, characterized in that the solvent of step a) is used in a ratio of between 300:1 and 50:1:1.

7. The process according to claim 6, characterized in that the solvent of step a) is used in a ratio of around 250:1.

8. Sodium risedronate in powdered amorphous form obtainable according to the process of claim 1.

9. Sodium risedronate in powdered amorphous form obtainable according to the process of claim 2.

10. Sodium risedronate in powdered amorphous form obtainable according to the process of claim 3.

11. Sodium risedronate in powdered amorphous form obtainable according to the process of claim 4.

12. Sodium risedronate in powdered amorphous form obtainable according to the process of claim 5.

13. Sodium risedronate in powdered amorphous form according to claim 8, characterized by an X-ray diffraction spectrum as represented in FIG. 1.

14. Sodium risedronate in powdered amorphous form characterized by an X-ray diffraction spectrum as represented in FIG. 1, wherein the sodium risedronate in amorphous form is prepared by the process according to claim 1.

15. A pharmaceutical composition comprising sodium risedronate in amorphous form according to claim 13 together with at least one pharmaceutically acceptable adjuvant.

16. The pharmaceutical composition according to claim 15, wherein the pharmaceutical composition is in the form of a tablet.

* * * * *